(12) United States Patent
Rasmussen et al.

(10) Patent No.: US 10,807,069 B2
(45) Date of Patent: Oct. 20, 2020

(54) HYDROPHOBIC MONOMERS, HYDROPHOBICALLY-DERIVATIZED SUPPORTS, AND METHODS OF MAKING AND USING THE SAME

(71) Applicant: 3M INNOVATIVE PROPERTIES COMPANY, St. Paul, MN (US)

(72) Inventors: Jerald K. Rasmussen, Woodville, WI (US); Cary A. Kipke, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 121 days.

(21) Appl. No.: 15/213,572

(22) Filed: Jul. 19, 2016

(65) Prior Publication Data

US 2016/0325268 A1    Nov. 10, 2016

Related U.S. Application Data (63) Continuation of application No. 13/258,018, filed as application No. PCT/US2010/027978 on Mar. 19, 2010.

(Continued)

(51) Int. Cl.
*B01J 20/285* (2006.01)
*C07C 237/22* (2006.01)
(Continued)

(52) U.S. Cl.
CPC .......... *B01J 20/285* (2013.01); *B01D 15/206* (2013.01); *B01D 15/327* (2013.01);
(Continued)

(58) Field of Classification Search
CPC ................ B01D 15/206; B01D 15/327; B01D 67/0006; B01D 67/0088; B01D 67/0093;
(Continued)

(56) References Cited

U.S. PATENT DOCUMENTS

| 2,701,809 A | 1/1951 | Plaut |
| 3,396,030 A | 8/1968 | Haas |

(Continued)

FOREIGN PATENT DOCUMENTS

| GB | 1108383 | 4/1968 |
| JP | S45-014031 | 5/1970 |

(Continued)

OTHER PUBLICATIONS

Ahuja, Santinder. Chiral separations by liquid chromatography. ACS Symposium Series; American Chemical Society: Washington DC, 1991, p. 1-26. (Year: 1991).*

(Continued)

*Primary Examiner* — Katherine Zalasky McDonald
(74) *Attorney, Agent, or Firm* — Julie Lapos-Kuchar

(57) ABSTRACT

A filtration media is disclosed comprising a hydrophobic monomer grafted onto a support, the hydrophobic monomer having the structure:

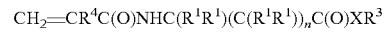

wherein n is an integer of 0 or 1; $R^1$ is independently selected from at least one of: a hydrogen atom, alkyls, aryls, and alkylaryls, wherein the alkyls, aryls, and alkylaryls have a total of 10 carbon atoms or less; $R^3$ is a hydrophobic group selected from at least one of: alkyls, aryls, alkylaryls and ethers, wherein the alkyls, aryls, alkylaryls and ethers have a total number of carbon atoms ranging from 4 to 30; $R^4$ is H or $CH_3$; X is O or NH. In some embodiments the hydrophobic monomer is derived from an amine or an alcohol ($HXR^3$) that has a hydrophilicity index of 25 or less. Such media may be used in applications such as hydrophobic interaction chromatography.

5 Claims, 2 Drawing Sheets

Related U.S. Application Data (60) Provisional application No. 61/165,132, filed on Mar. 31, 2009.

(51) Int. Cl.

| | | |
|---|---|---|
| *C08F 20/54* | (2006.01) | |
| *B01D 71/56* | (2006.01) | |
| *B01J 20/286* | (2006.01) | |
| *B01D 67/00* | (2006.01) | |
| *B01D 69/12* | (2006.01) | |
| *B01D 15/20* | (2006.01) | |
| *B01D 15/32* | (2006.01) | |

(52) U.S. Cl.
CPC ..... *B01D 67/0006* (2013.01); *B01D 67/0088* (2013.01); *B01D 67/0093* (2013.01); *B01D 69/125* (2013.01); *B01D 71/56* (2013.01); *B01J 20/286* (2013.01); *C07C 237/22* (2013.01); *C08F 20/54* (2013.01); *B01D 2323/30* (2013.01); *B01D 2325/38* (2013.01)

(58) Field of Classification Search
CPC .. B01D 69/125; B01D 71/56; B01D 2323/30; B01D 2325/38; B01J 20/285; B01J 20/286; B01J 20/287
See application file for complete search history.

(56) References Cited

U.S. PATENT DOCUMENTS

| | | | |
|---|---|---|---|
| 3,452,182 A | 6/1969 | Haas | |
| 3,713,834 A | 1/1973 | Fitzgerald | |
| 3,721,565 A | 3/1973 | Fitzgerald | |
| 3,850,646 A | 11/1974 | Wagner | |
| 4,094,833 A | 6/1978 | Johansson | |
| 4,304,705 A | 12/1981 | Heilmann | |
| 4,395,524 A | 7/1983 | Emmons | |
| 4,451,619 A | 5/1984 | Heilmann | |
| 4,520,182 A | 5/1985 | Turner | |
| 4,521,580 A | 6/1985 | Turner | |
| 4,528,348 A | 7/1985 | Turner | |
| 4,730,028 A | 3/1988 | Bock | |
| 4,761,233 A * | 8/1988 | Linder | B01D 67/0011 210/500.37 |
| 4,871,824 A | 10/1989 | Heilmann | |
| 4,981,935 A | 1/1991 | Bock | |
| 5,030,352 A | 7/1991 | Varady | |
| 5,094,960 A | 3/1992 | Bonomo | |
| 5,274,167 A | 12/1993 | Lange | |
| 5,344,701 A | 9/1994 | Gagnon | |
| 5,403,902 A | 4/1995 | Heilmann | |
| 5,429,746 A | 7/1995 | Shadle | |
| 5,453,186 A | 9/1995 | Muller | |
| 5,468,847 A | 11/1995 | Heilmann | |
| 5,503,933 A | 4/1996 | Afeyan | |
| 5,561,097 A | 10/1996 | Gleason | |
| 5,641,403 A | 6/1997 | Muller | |
| 5,641,870 A | 6/1997 | Rinderknecht | |
| 5,647,987 A | 7/1997 | Muller | |
| 5,667,692 A | 9/1997 | Muller | |
| 5,993,935 A | 11/1999 | Rasmussen | |
| 6,420,028 B1 | 7/2002 | Hagen | |
| 6,479,300 B1 * | 11/2002 | Jiang | B01D 15/3828 210/198.2 |
| 6,559,334 B1 | 5/2003 | Lange | |
| 6,689,854 B2 | 2/2004 | Fan | |
| 2005/0159569 A1 | 7/2005 | Fansler | |
| 2007/0154703 A1 | 7/2007 | Waller | |
| 2008/0014625 A1 * | 1/2008 | Etzel | A61L 2/0017 435/239 |

FOREIGN PATENT DOCUMENTS

| | | |
|---|---|---|
| JP | WO 96/24074 | 8/1996 |
| JP | H11-510494 | 9/1999 |
| JP | 2000-500450 | 1/2000 |
| JP | 2008-514782 | 5/2008 |
| JP | 2008-514788 | 5/2008 |
| JP | 2011-525942 | 9/2011 |
| WO | WO 96/24644 | 8/1996 |
| WO | WO 97/05101 | 2/1997 |
| WO | WO 97/18186 | 5/1997 |
| WO | WO 2001/30872 | 5/2001 |
| WO | WO 2006/039064 | 4/2006 |
| WO | WO 2006/039141 | 4/2006 |
| WO | WO 2009/158071 | 12/2009 |

OTHER PUBLICATIONS

Boudreaux, "Controlled activity polymers. IX copolymers of acrylic acid and isomeric N-alkylacrylamide monomers with pendent β-naphthol ester moieties: Hydrolytic release studies", *Journal of Controlled Release*, 1996, vol. 40, pp. 235-243.

Carrilho, "Rapid DNA Sequencing of More Than 1000 Bases per Run by Capillary Electrophoresis Using Replaceable Linear Polyacrylamide Solutions," *Analytical Chemistry*, Oct. 1, 1996, vol. 68, No. 19, pp. 3305-3313.

Hubner, "Synthese and Reaktionen von 2-Alkenyloxazolonen," *Die Angewandte Makromolekulare Chemie*, 1970, vol. 11, No. 124, pp. 109-124.

IDE, Bulletin of the Chemical Society of Japan, (2001), 74(7), 1355-1359.

IDE, "Estimation of Molecular Environment for Amino Acids in Proteins by Monolayer Behaviors of the Amino Acid Derivative Polymers on a Water Surface", *Langmuir*, 2001, vol. 17, No, 8, pp. 2493-2496.

Iwakura, et al., "A Novel Preparation of Pseudoxazolones," *Tetrahedron*, vol. 23, Iss. 8, (1967) pp. 3363-333.

Kinsinger, Langmuir, (2008), 24(23), 13231-13236).

Messman, "Highly Tailorable Materials based on 2-Vinyl-4,4-dimethyl Azlactone: (Co)Polymerization, Synthetic Manipulation and Characterization", *Macromolecules*, Jun. 23, 2009, vol. 42, No. 12, pp. 3933-3941.

Sherrington, "Preparation, structure and morphology of polymer supports", *Chemical Communications*, 1998, Issue 21, p. 2275-2286.

Taylor, "Preparation of Films Exhibiting a Balanced Temperature Dependence to Permeation by Aqueous Solutions—A Study of Lower Consolute Behavior", *Journal of Polymer Science, Polymer Chemistry Edition*, Nov. 1975, vol. 13, Issue 11, pp. 2551-2570.

Taylor, "The Synthesis of Vinyl Peptide Monomers", *Journal of Polymer Science, Part B: Polymer Letters*, Aug. 1969, vol. 7, No. 8, pp. 597-603.

International Search Report for PCT/US2010/027978, 5 pgs.

Written Opinion of the ISA for International Application No. PCT/US2010/027978, 6 pgs.

* cited by examiner

HYDROPHOBIC MONOMERS, HYDROPHOBICALLY-DERIVATIZED SUPPORTS, AND METHODS OF MAKING AND USING THE SAME

CROSS REFERENCE TO RELATED APPLICATIONS

This application is a continuation of U.S. application Ser. No. 13/258,018, filed Sep. 21, 2011, which is a national stage filing under 35 U.S.C. 371 of PCT/US2010/027978, filed Mar. 19, 2010, which claims priority to U.S. Provisional Application No. 61/165,132, filed Mar. 31, 2009, the disclosure of which is incorporated by reference in its/their entirety herein.

TECHNICAL FIELD

The present disclosure generally relates to hydrophobic monomers, and their use, for example, in hydrophobically-derivatized supports. The present disclosure also generally relates to the method of making and using these hydrophobically-derivatized supports in applications such as hydrophobic interaction chromatography.

BACKGROUND

Hydrophobic interaction chromatography (HIC) is a chromatography technique based on the separation of molecules based on their hydrophobicity. Generally, sample molecules in a high salt buffer are loaded on the HIC column. The salt in the buffer interacts with water molecules to reduce the solvation of the sample molecules in solution, thereby exposing hydrophobic regions in the sample molecules, which are consequently adsorbed by the stationary phase of the HIC column. The more hydrophobic the molecule, the less salt needed to promote binding. Usually, a decreasing salt gradient is used to elute samples from the column in order of increasing hydrophobicity. Sample elution may also be achieved by the addition of mild organic modifiers (e.g., solvents) or detergents to the elution buffer, by changing the pH, or by the addition of chaotropic agents.

The HIC stationary phase typically comprises agarose, silica, or organic polymer resins, which may be modified by hydrophobic ligands. One such HIC stationary phase is prepared by reacting a hydrophobic ligand comprising a nucleophile, to a particle (e.g., a bead) comprising an azlactone moiety. For example, U.S. Pat. No. 5,993,935 (Rasmussen et al.) describes the covalent bonding of azlactone moieties on the surface of particles with nucleophilic ligands by direct interaction (i.e., without the need for an intermediate activation step).

U.S. Pat. No. 5,561,097 (Gleason, et al.) describes a method of controlling the density of low molecular weight ligands, which are covalently bonded to azlactone moieties on the surface of supports (e.g., particles). The density is controlled by conducting the covalent bonding reaction in the presence of a quencher. The azlactone-functionalized support is typically prepared by polymerization of an azlactone monomer or precursor to a support with subsequent cyclization to the azlactone. The azlactone-functionalized support is then reacted with a ligand (such as benzyl amine) to produce a derivatized support. Although extremely low levels of side reactions such as hydrolysis take place during the course of the derivatization reaction, some hydrolysis of the azlactone may indeed take place, generating carboxylic acid groups. When the end product is an ion exchange resin, this minor amount of side reaction is not a concern. However, in some applications, such as HIC stationary phases, the presence of any ionic functionality, even trace amounts, can lead to changes in performance, for example, in dynamic binding capacity and/or resolution.

HIC stationary phases are also susceptible to hydrolysis when exposed to basic conditions if they are derived from hydrophobic (meth)acrylate esters and/or (meth)acrylamide monomers. For example, one molar sodium hydroxide is often used to clean chromatography columns between uses, however these basic conditions can hydrolize the (meth)acrylate ester and/or (meth)acrylamide polymer. This hydrolysis leads to the formation of carboxylic acid functionality on the support, and thus to a degradation in chromatographic performance.

SUMMARY

In one aspect, the present disclosure provides filtration media comprising a porous support with a hydrophobic monomer grafted thereon, the hydrophobic monomer having the structure:

$$CH_2=CR^4C(O)NHC(R^1R^1)(C(R^1R^1))_nC(O)NHR^3$$

wherein n is an integer of 0 or 1; $R^1$ is independently selected from: alkyls, aryls, and alkylaryls, wherein the alkyls, aryls, and alkylaryls have a total of 10 carbon atoms or less; $R^3$ is a hydrophobic group selected from: alkyls, aryls, alkylaryls and ethers, wherein the alkyls, aryls, alkylaryls and ethers have a total number of carbon atoms ranging from 4 to 30; $R^4$ is H or $CH_3$; wherein the hydrophobic monomer is derived from an amine ($HNR^3$) that has a hydrophilicity index of 25 or less.

In another aspect, the present disclosure provides a composition comprising a hydrophobic monomer having the structure:

$$CH_2=CR^4C(O)NHC(R^2)(C(R^1R^1))_nC(O)NHR^3$$

wherein n is an integer of 0 or 1; $R^1$ is independently selected from: alkyls, aryls, and alkylaryls, wherein the alkyls, aryls, and alkylaryls have a total of 10 carbon atoms or less; $R^2$ is selected from alkyls, aryls, and alkylaryls, wherein the alkyls, aryls, and alkylaryls have a total of 10 carbon atoms or less; $R^3$ is a hydrophobic group selected from: alkyls, aryls, alkylaryls and ethers, wherein the alkyls, aryls, alkylaryls and ethers have a total number of carbon atoms ranging from 4 to 30; $R^4$ is H or $CH_3$; wherein the hydrophobic monomer is derived from an amine ($HNR^3$) that has a hydrophilicity index of 25 or less.

In yet another aspect, method of separating biomacromolecules is described, the method comprising:

contacting a solution comprising biomacromolecules to a hydrophobically-derivatized support, wherein the hydrophobically-derivatized support comprises a support grafted with a hydrophobic monomer of the following structure:

$$CH_2=CR^4C(O)NHC(R^1R^1)(C(R^1R^1))_nC(O)NHR^3$$

wherein n is an integer of 0 or 1; $R^1$ is independently selected from: alkyls, aryls, and alkylaryls, wherein the alkyls, aryls, and alkylaryls have a total of 10 carbon atoms or less; $R^3$ is a hydrophobic group selected from: alkyls, aryls, alkylaryls and ethers, wherein the alkyls, aryls, alkylaryls and ethers have a total number of carbon atoms ranging from 4 to 30; $R^4$ is H or $CH_3$; wherein the hydrophobic monomer is derived from an amine ($HNR^3$) that has a hydrophilicity index of 25 or less.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "a", "an", and "the" are used interchangeably with "at least one" to mean one or more of the elements being described.

The term "and/or" means one or all of the listed elements or a combination of any two or more of the listed elements.

The term "alkyl" refers to a monovalent group that is a radical of an alkane, which is a saturated hydrocarbon. The alkyl can be linear, branched, cyclic, or combinations thereof and typically has 1 to 30 carbon atoms. In some embodiments, the alkyl group contains at least 1, 2, 3, 4, 5, 6, 8, 10, 15, 20, or 25 carbon atoms; at most 30, 28, 26, 25, 20, 15, 10, 8, 6, 5, 4, or 3 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkylene" refers to a divalent group that is a radical of an alkane. The alkylene can be straight-chained, branched, cyclic, or combinations thereof. The alkylene often has 1 to 30 carbon atoms. In some embodiments, the alkylene group contains at least 1, 2, 3, 4, 5, 6, 8, 10, 15, 20, or 25 carbon atoms; at most 30, 28, 26, 25, 20, 15, 10, 8, 6, 5, 4, or 3 carbon atoms. The radical centers of the alkylene can be on the same carbon atom (i.e., an alkylidene) or on different carbon atoms.

The term "aryl" refers to a monovalent group that is aromatic and carbocyclic or heterocyclic. The aryl can have one to five rings that are connected to or fused to the aromatic ring. The other ring structures can be aromatic, non-aromatic, or combinations thereof and typically has 1 to 30 carbon atoms. In some embodiments, the aryl group contains at least 1, 2, 3, 4, 5, 6, 8, 10, 15, 20, or 25 carbon atoms; at most 30, 28, 26, 25, 20, 15, 10, 8, 6, 5, 4, or 3 carbon atoms. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "alkylaryl" refers to a monovalent group that is a combination of an alkyl and an aryl group. The alkylaryl can be an aralkyl, that is, an alkyl substituted with an aryl, or alkaryl, that is, an aryl substituted with an alkyl. The alkylaryl can have one to five rings that are connected to or fused to the aromatic ring and can comprise linear, branched, or cyclic segments, or combinations thereof. The alkylaryl group typically has 1 to 30 carbon atoms. In some embodiments, the alkylaryl group contains at least 1, 2, 3, 4, 5, 6, 8, 10, 15, 20, or 25 carbon atoms; at most 30, 28, 26, 25, 20, 15, 10, 8, 6, 5, 4, or 3 carbon atoms.

The term "(meth)acrylamide" refers to compounds containing either an acrylamide or a methacrylamide structure or combinations thereof. Similarly, the term "(meth)acrylate" refers to compounds containing either an acrylate or a methacrylate structure or combinations thereof.

The terms "polymer" and "polymeric material" refer to both materials prepared from one monomer such as a homopolymer or to materials prepared from two or more monomers such as a copolymer, terpolymer, etc. Likewise, the term "polymerize" refers to the process of making a polymeric material that can be a homopolymer, copolymer, terpolymer, or the like. The terms "copolymer" and "copolymeric material" refer to a polymeric material prepared from at least two monomers and includes terpolymers, quadpolymers, etc.

The terms "room temperature" and "ambient temperature" are used interchangeably to mean temperatures in the range of 20° C. to 25° C.

The above summary of the present disclosure is not intended to describe each disclosed embodiment or every implementation of the present disclosure. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

DETAILED DESCRIPTION

There is a need to synthesize hydrophobic free-radically polymerizable (meth)acrylamide monomers that are easily synthesized and isolated. Additionally, there is a need to manufacture a polymer support that comprises hydrophobic character with reduced ionic character. There is also a need to manufacture hydrophobic supports, which, for example, can be used as an HIC stationary phase, that have both high dynamic binding capacity and good protein resolution characteristics.

This disclosure provides hydrophobic free-radically polymerizable (meth)acrylamide monomers. In some embodiments, these hydrophobic free radically polymerizable (meth)acrylamide monomers can be polymerized with other monomers to produce hydrophobic supports. In some embodiments, these hydrophobic supports may be used to separate biological and non-biological samples.

The hydrophobic monomers according to this disclosure have the structure according to formula (I):

$$CH_2=CR^4C(O)NHC(R^1R^1)(C(R^1R^1))_nC(O)XR^3 \qquad (I)$$

wherein n is an integer of 0 or 1; $R^1$ is independently selected from at least one of a hydrogen atom, alkyls, aryls, and alkylaryls; $R^3$ is a hydrophobic group selected from at least one of: alkyls, aryls, alkylaryls and ethers; $R^4$ is H or $CH_3$; and X is O or NH.

In one embodiment, the hydrophobic monomer is derived from an amine or alcohol ($HXR^3$) that has a hydrophilicity index of 25 or less.

In one embodiment, $R^1$ is independently selected from at least one of: hydrogen atoms, alkyls, aryls, and alkylaryls, wherein the alkyls, aryls, and alkylaryls have a total of 10 carbon atoms or less, 9 carbon atoms or less, 8 carbon atoms or less, 7 carbon atoms or less, 6 carbon atoms or less, 5 carbon atoms or less, 4 carbon atoms or less, or even 3 carbon atoms or less. Examples of $R^1$ include: a hydrogen atom, a methyl group, an ethyl group, and a phenyl group.

In one embodiment, $R^3$ is a hydrophobic group selected from at least one of: alkyls, aryls, alkylaryls and ethers, wherein the alkyls, aryls, alkylaryls and ethers have a total number of carbon atoms ranging from 4 to 30. In some embodiments, the alkyls, aryls, alkylaryls and ethers contain at least 4, 5, 6, 8, 10, 12, 15, or 20 carbon atoms; at most 30, 28, 26, 24, 20, 15, 12, 10, 8, or 6 carbon atoms. Examples of $R^3$ include: a benzyl group, a phenethyl group, a phenoxyethyl group, a phenylpropyl group, a butyl group, a pentyl group, a hexyl group, an octyl group, a dodecyl group, an octadecyl group, and a phenylbutyl group.

The hydrophobic monomers of this disclosure are synthesized at room temperature by a nucleophilic reaction between an alkenyl azlactone with a primary amine or alcohol ligand. The alkenyl azlactone includes 5-member and 6-member azlactones with an alkenyl substituent, such as those disclosed in formulas (II) and (III) below, wherein $R^1$ and $R^4$ are the same as those defined above.

Exemplary alkenyl azlactones include: 4,4-dimethyl-2-vinyl-4H-oxazol-5-one (vinyldimethylazlactone), 2-isopropenyl-4H-oxazol-5-one, 2-vinyl-4,5-dihydro-[1,3]oxazin-6-one, 4,4-dimethyl-2-vinyl-4,5-dihydro-[1,3]oxazin-6-one, 4,5-dimethyl-2-vinyl-4,5-dihydro-[1,3]oxazin-6-one, and combinations thereof.

During the synthesis of the hydrophobic monomer, the primary amine or alcohol reacts with the carbonyl of the alkenyl azlactone, opening the azlactone ring and forming an adduct. The reaction solvent can be organic (such as alcohols, ethers, hydrocarbons, esters, halogenated solvents, or combinations thereof), aqueous, or mixed, but should be capable of dissolving or at least partially dissolving the alkenyl azlactone and the primary amine or alcohol ligand. Although the azlactone moiety is quite stable towards hydrolysis, it is known that ring opening by water can occur as a minor side-reaction. This hydrolysis can lead to the formation of carboxyl groups, which may impart ionic character. Therefore, in one embodiment, the covalent bonding of the alkenyl azlactone with the primary amine or alcohol ligand is conducted in an organic solvent to ensure little to no hydrolysis of the alkenyl azlactone.

The azlactone moiety reacts rapidly with the primary amine or alcohol of the ligand forming a direct covalent bond with no displacement of a by-product molecule. Thus, purification of the resulting hydrophobic monomer is minimized. Typically, the hydrophobic monomer precipitates from the reaction solvent in very pure form (for example, greater than 90% purity, or even greater than 99% purity) and can be isolated by simple filtration and drying. Optionally, the hydrophobic monomer can be recrystallized to further enhance its purity, although this is generally not necessary.

For purposes of this disclosure, the selection of the primary amine or alcohol ligand utilized in the synthesis of the hydrophobic monomer will determine the hydrophobicity of the resulting hydrophobic monomer. The primary amine or alcohol ligand comprises a hydrophobic group selected from at least one of: alkyls, aryls, alkylaryls and ethers, wherein the alkyls, aryls, alkylaryls and ethers have a total number of carbon atoms ranging from 4 to 30. In some embodiments, the alkyls, aryls, alkylaryls and ethers contain at least 4, 5, 6, 8, 10, 12, 15, or 20 carbon atoms; at most 30, 28, 26, 24, 20, 15, 12, 10, 8, or 6 carbon atoms.

In one embodiment, the hydrophobic monomer has a calculated hydrophilicity index (HI) of 25 or less, 20 or less, 15 or less, or even 10 or less. The HI is an empirical concept that is described in detail in U.S. Pat. No. 4,451,619 (Heilmann, et al.), herein incorporated by reference. In general, this concept allows one to determine the effect that an added primary amine or alcohol ligand will have on the hydrophilicity or hydrophobicity of the final product, (i.e., a hydrophobic monomer, a polymerizable mixture, or a hydrophobically-derivatized support). For purposes of this disclosure, HI is calculated based on the primary amine or alcohol ligand of $R^3$ (i.e., $HXR^3$). The HI of the hydrophobic monomer according to this disclosure is defined as:

$$HI = \frac{\text{total molecular weight of the hydrophilic groups in } HXR^3}{\text{molecular weight of } HXR^3} \times 100$$

The hydrophilic groups are generally those that are functionally capable of forming hydrogen bonds with water. Examples of hydrophilic groups include: —N—, —NH—, —NH$_2$, —OH, —O—, C=O, —CO$_2$H, —CO$_2^-$ M$^+$ (where M$^+$ is an alkali or alkaline earth metal ion), —SO$_3$H, —SO$_3^-$ M$^+$, —CONH2, —SH, —NR$_3^+$ X$^-$ (where R=C$_{1-4}$ alkyl and X$^-$ is typically a halide), —NHCONH—, and the like.

Primary amine or alcohol ligands that tend to impart a hydrophilic character to final product typically have an HI of greater than 30, while the primary amine or alcohol ligands that impart a hydrophobic character typically have an HI of less than 20. Primary amine or alcohol ligands with an HI between 20 and 30 are typically classified as "neutral" or "borderline".

Table 1 lists the HI of a number of primary amine and alcohol ligands that have been found to be useful for the purposes of this disclosure. Interestingly, some ligands having a "borderline" HI (for example, butylamine and phenoxyethylamine) can be used in applications such as protein purification.

TABLE 1

Hydrophilicity Index for Primary Amine Ligands

| Ligands | Total Molecular weight | Hydrophilic Component MW | HI |
|---|---|---|---|
| Benzylamine | 107 | 16 | 15 |
| Phenethylamine | 121 | 16 | 13 |
| Phenoxyethylamine | 137 | 32 | 23 |
| Phenylpropylamine | 135 | 16 | 12 |
| Phenylbutylamine | 149 | 16 | 11 |
| Butylamine | 73 | 16 | 22 |
| Hexylamine | 101 | 16 | 16 |
| Octylamine | 129 | 16 | 12 |
| Octadecylamine | 270 | 16 | 6 |
| Phenylbutanol | 150 | 17 | 11 |

In some applications, hydrophobic monomers derived from primary amine ligands are preferred over those derived from alcohols due to the presence of two amide functional groups, which result in a lower susceptibility towards hydrolysis.

Exemplary hydrophobic monomers include:

$CH_2$=$CHC(O)NHC(CH_3)(CH_3)C(O)NH(CH_2)_4C_6H_5$;
$CH_2$=$CHC(O)NHC(CH_3)(CH_3)C(O)O(CH_2)_4C_6H_5$;
$CH_2$=$CHC(O)NHC(CH_3)(CH_3)C(O)NHCH_2C_6H_5$;
$CH_2$=$CHC(O)NHC(CH_3)(CH_3)C(O)NH(CH_2)_2C_6H_5$;
$CH_2$=$CHC(O)NHC(CH_3)(CH_3)C(O)NH(CH_2)_2OC_6H_5$;
$CH_2$=$CHC(O)NHC(CH_3)(CH_3)C(O)NH(CH_2)_3C_6H_5$;
$CH_2$=$CHC(O)NHC(CH_3)(CH_3)C(O)NH(CH_2)_3CH_3$;
$CH_2$=$CHC(O)NHC(CH_3)(CH_3)C(O)NH(CH_2)_5CH_3$;
$CH_2$=$CHC(O)NHC(CH_3)(CH_3)C(O)NH(CH_2)_7CH_3$;
$CH_2$=$CHC(O)NHC(CH_3)(CH_3)C(O)NH(CH_2)_{11}CH_3$;
$CH_2$=$CHC(O)NHC(CH_3)(CH_3)C(O)NH(CH_2)_{17}CH_3$; or combinations thereof.

The hydrophobic monomers of this disclosure may have a tendency in solution to self-associate or, when in the presence of other monomers or polymers, associate with the other monomers or polymers. This association can be the result of two separate interactions. First, the hydrophobic groups of the hydrophobic monomers may associate with one another, or with the other monomers or polymers, especially in aqueous media. Secondly, hydrogen-bonding interactions can occur between the amide functionalities of the hydrophobic monomers or between the hydrophobic monomers and the other monomers or polymers. The hydrogen-bonding interactions are particularly prevalent with the hydrophobic monomers derived from amine ligands, wherein two amide groups are present. The tendency of the hydrophobic monomers to associate may be advantageous, for example, enabling one to control a polymer microstructure (such as, for example, the distribution of hydrophobic groups within a polymerized support) and/or the properties of the final product (such as, for example, hydrophobicity and/or viscosity) by manipulating the polymerization conditions.

In addition to the hydrophobic portion, which can participate in hydrophobic interactions, the hydrophobic monomer also comprises an unsaturated site (e.g., a double bond), which is derived from the alkenyl substituent of the alkenyl azlactone. In one aspect of this disclosure, this site of unsaturation enables the hydrophobic monomer to participate in free radical polymerization schemes. Thus, these hydrophobic monomers may be added to a polymerizable mixture, which then may be used to make a hydrophobically-derivatized support.

In one aspect, the polymerizable mixture comprises the hydrophobic monomer.

In one embodiment, the polymerizable mixture further comprises a cross-linking monomer. The cross-linking monomer comprises a plurality of polymerizable groups, which during polymerization, extend the chain length of the polymer backbone and during curing, physically join (or cross-link) the polymer backbones. Cross-linking aids in the mechanical stability of the resulting article.

The cross-linking monomers include, for example, N,N'-alkylenebis(meth)acrylamides, alkylenebis(meth)acrylates, divinylaromatics, polyallylesters or combinations thereof. Exemplary cross-linking monomers include: ethylenically unsaturated esters such as ethylene diacrylate, ethylene dimethacrylate, trimethylolpropane triacrylate and trimethacrylate; and α- and β-unsaturated amides, such as methylene bis(acrylamide), methylene bis(methacrylamide), N,N'-diacryloylpiperazine, N,N'-diacryloyl-1,2-diaminoethane, and N,N'-dimethacryloyl-1,2-diaminoethane; or combinations thereof. In some applications, such as HIC-type applications, the N,N'-alkylenebis(meth)acrylamides are preferred due to their hydrophilicity and increased hydrolytic stability.

In one embodiment, the polymerizable mixture further comprises a non-cross-linking monomer. The non-cross-linking monomer is used to propagate the polymer backbone (i.e., extend the chain length), but does not generally participate in physically joining polymer backbones or may be used to solubilize the hydrophobic monomer. In one embodiment, the non-cross-linking monomers are uniformly distributed throughout the hydrophobically-derivatized support and assist in uniformly distributing the hydrophobic monomers in the hydrophobically-derivatized support.

The non-cross-linking monomers include: (meth)acrylate, (meth)acrylamide monomers, or combinations thereof. Exemplary non-cross-linking monomers include: dimethylacrylamide, acrylamide, methacrylamide, hydroxyethyl (meth)acrylate, or combinations thereof. The use of these non-cross-linking monomers can provide significant enhancements to the properties of the hydrophobically-derivatized support. For example, although not wanting to be bound by theory, the concentration and type of non-cross-linking monomers are thought to influence the porosity of the hydrophobically-derivatized support and/or the distribution of the hydrophobic monomer.

In one embodiment, the hydrophobic monomers of formula (I) and non-crosslinking monomers may be used in the preparation of hydrophobically-associating polymers, which are useful as aqueous fluid rheology or flow modifiers. In one embodiment, these hydrophobically-associating polymers may be used, for example, as flocculation aids for waste water treatment and dewatering sludge, and for rheology control for secondary and tertiary oil recovery. In another embodiment, these hydrophobically-associating polymers may also be used as separation media for capillary electrophoresis in DNA or RNA sequencing and separations.

The amount of hydrophobic monomer, cross-linking monomer, and/or non-cross-linking monomer may be important in the properties of the polymerized mixture and the resulting hydrophobically-derivatized support. Generally, the amount of hydrophobic monomer added controls the hydrophobicity of the resulting hydrophobically-derivatized support. The hydrophobic monomer can be added at 0.1 to 30% by weight relative to the total monomer amount. In some embodiments, the hydrophobic monomer is at least 0.1, 0.2, 0.5, 1, 1.5, 3, 5, 10, 15, 20, or 25% by weight; at most 30, 25, 20, 15, 10, 5, 3, 1.5, 1, 0.5% by weight relative to the total monomer amount. Generally, the amount of cross-linking monomer added controls the rigidity and swelling ability of the particle. The cross-linking monomer can be added at 0-99.9% by weight relative to the total monomer amount. In some embodiments, the cross-linking monomer is at least 0, 0.1, 0.5, 1, 1.5, 3, 5, 10, 20, 30, 40, 50, 60, 70, 80, 90, 95, or 98% by weight; at most 99.9, 99.5, 99, 98, 95, 90, 80, 75, 70, 60, 50, 40, 30, 20, 10, 5, 3, 1, or 0.5% by weight relative to the total monomer amount. Generally, the amount of non-cross-linking monomer aids in the determination of final copolymer properties, including hydrophilicity, solubility, porosity, crosslink density, rigidity, etc., depending upon the final application. The non-cross-linking monomer may be added at 0-99.9% by weight relative to total monomer amount. In some embodiments, the non-cross-linking monomer is at least 0, 0.1, 0.5, 1, 1.5, 3, 5, 10, 20, 30, 40, 50, 60, 70, 80, 90, 95, or 98% by weight; at most 99.9, 99.5, 99, 98, 95, 90, 80, 75, 70, 60, 50, 40, 30, 20, 10, 5, 3, 1, or 0.5% by weight relative to the total monomer amount.

In one embodiment, the amount of the cross-linking monomer is greater than the amount of the non-cross-linking monomer. In one embodiment, the amount of the non-cross-linking monomer is greater than the amount of the hydrophobic monomer. In yet another embodiment, the amount of the cross-linking monomer is greater than the amount of the non-cross-linking monomer, which is greater than the amount of the hydrophobic monomer. For example, in an HIC application, the amount of cross-linking monomer is 60% or more by weight relative to the total monomer amount to enable rigidity of the hydrophobically-derivatized support to withstand the pressure tolerances, and the amount of hydrophobic monomer is 10% or less by weight relative to the total monomer amount to ensure release of the analyte from the HIC stationary phase.

In another embodiment, the polymerizable mixture may comprise a porogen. A porogen may be added to the polymerizable mixture to control the pore structure of the hydrophobically-derivatized support, especially when the hydrophobically-derivatized support is a particle or a coating.

Pore formation or porosity in polymeric materials is described in detail by Sherrington, *Chem. Commun.,* 2275-2286 (1998). With some materials, especially gel-type materials, porosity is formed during the polymerization or curing process as a result of the entanglement and/or crosslinking of the polymer chains. Typically this porosity is very low or nonexistent unless the polymer network is highly swollen by a solvent. Alternately, porogens can be added to the composition to create permanent pores. Added porogens typically influence the timing of phase separation of the forming polymer network from the rest of the monomer phase mixture. Examples of porogens include: water, alcohols (such as, for example, methanol, ethanol, and isopropanol), ethylene glycol, propylene glycol, polyols having at least three hydroxy groups (such as, for example, glycerol, inositol, glucose, sucrose, maltose, dextran, pentaerithritol, trimethylolethane, timethylolpropane, dipentaerithritol, and tripentaerithritol), and polymeric porogens (such as, for example, polyethylene glycol, polypropylene glycol, polyacrylic acid, polysaccharide, and the like), dispersed organic aggregate (such as, for example, ethoxylated hydrocarbons), or combinations thereof.

Other factors may also be important in controlling the pore structure of the hydrophobically-derivatized support including, for example, the interaction between the co-monomer composition and the selection of the porogen(s), the mass ratio between the non-cross-linking monomer and the cross-linking monomer, the chemical structure of the non-cross-linking monomer, or combinations thereof.

As mentioned above, the polymerizable mixture may be used to form a hydrophobically-derivatized support. This hydrophobically-derivatized support may be obtained by at least one of: graft polymerizing the polymerizable mixture onto a substrate, coating the polymerizable mixture onto a substrate and polymerizing the polymerizable mixture on the surfaces of the substrate, or polymerizing and cross-linking the polymerizable mixture to form particles, which may be used as supports themselves or may added to other porous substrates.

The degree of hydrophobicity of the hydrophobically-derivatized support is controlled by the nature of the hydrophobic ligand, the amount of hydrophobic ligand present on the support surface, and/or the distribution of the hydrophobic groups on the support surface (which in the case of hydrophobically-derivatized particles, is controlled primarily by pore structure and swell volume of the particle).

In one embodiment, the surface of a pre-existing support is exposed to high energy radiation to generate free radical reaction sites on the surface as disclosed in U.S. Pat. No. 5,344,701 (Gagnon et al.). Exposure of the pre-existing support with the polymerizable mixture can take place simultaneously with or subsequent to the irradiation of the pre-existing support. Depending on the type of radiation and other process conditions, the polymerizable mixture can either be grafted to the surface of the pre-existing support or can be formed as a coating on the pre-existing support or can become particles enmeshed within void spaces of the support. In the former instance, the hydrophobic monomer is covalently bound to the pre-existing support. The pre-existing support may be treated with plasma, corona, beta, gamma, electron-beam, x-ray, ultraviolet, and other electromagnetic radiation as is known in the art. The radiation may occur in the presence of other compounds, such as, for example, oxygen, or photoinitiators. The pre-existing supports, depending on the final use, may be porous or non-porous, continuous or non-continuous, and flexible or inflexible. Examples of pre-existing supports may include: woven webs, nonwoven webs, fibrous webs, microporous membranes, fibers, hollow fibers, tubes, microporous films, nonporous films, or combinations thereof. The pre-existing supports may be made from a variety of materials including ceramics, glass, metallic, polymeric materials, or combinations thereof. Examples of suitable polymeric materials include: polyalkylenes such as polyethylene and polypropylene; halogenated polymers such as polyvinyl chloride and polyvinylidene fluoride; polyamides such as nylons; polystyrenes; poly(ethylene vinyl acetate); polyacrylates such as polymethyl methacrylate; polycarbonate; cellulosics such as cellulose acetate butyrate; polyesters such as poly (ethylene teraphthalate); poly imidines; polyurethanes; or combinations thereof.

In another embodiment, the polymerizable mixture is coated onto the surface of a pre-existing support. Typically, the alkenyl moiety of the hydrophobic monomer is not covalently bound to the surface of the pre-existing support, therefore, the polymerizable mixture also comprises a cross-linking monomer and optionally a non-cross-linking monomer to cross-link the polymerizable mixture onto the pre-existing support. The pre-existing supports are similar to those described above. The polymerization and resultant cross-linking may be initiated by chemical and/or physical means including, for example, redox chemistry, thermal initiation, UV irradiation or by ionizing radiation (such as, for example, e-beam and gamma radiation), or by other means as is well known in the art.

In one embodiment, the hydrophobic monomer is polymerized to produce hydrophobically-derivatized particles. The hydrophobic monomer, a cross-linking monomer, and optionally a non-cross-linking monomer are mixed together and polymerized as an inverse suspension. As is apparent to one skilled in the art, the initiation system, suspending medium, stirring rate and the suspending agent are all essentially independent and important variables in the polymerization process. In one embodiment, the monomers are dissolved in a water/alcohol solution, this solution is suspended as droplets in an organic, immiscible medium, and sodium persulfate and tetramethylethylenediamine are used to initiate the polymerization. Substitution of the various components by comparable materials can certainly be made, and such substitutions would not be outside the spirit and scope of the present disclosure.

The hydrophobically-derivatized particles of this disclosure can have a spherical shape, a regular shape, or an irregular shape. Size of the azlactone-derived functionalized particles can vary widely within the scope of the disclosure. Generally the size of the azlactone-derived functionalized particles ranges from 0.1 micrometer (µm) to 5 millimeters (mm) in average diameter.

In one embodiment, the hydrophobically-derivatized particles are confined. For example, the hydrophobically-derivatized particles can be placed in a vessel (such as a tube), enclosing at least one end of the vessel with a frit to create a chromatographic column. Suitable columns are known in the art and can be constructed of such materials as glass, polymeric material, stainless steel, titanium and alloys thereof, or nickel and alloys thereof. Methods of filling the column to effectively pack particles in the column are known in the art. The chromatographic column, when packed with the hydrophobically-derivatized particles, can be used in HIC applications.

Although the average particle size in chromatography can be as large as 2000 micrometers, the average particle size is typically no greater than 500 micrometers. If the average particle size is larger than about 500 micrometers, the efficiency of the chromatographic process may be low, especially for the purification or separation of large biomacromolecules such as proteins that often have low diffusion rates into the pores of chromatographic particles.

In another embodiment, the hydrophobically-derivatized particles are dispersed within a continuous, porous matrix. The continuous, porous matrix is typically at least one of a woven or non-woven fibrous web, porous fiber, porous membrane, porous film, hollow fiber, film, or tube. Suitable continuous, porous matrixes are further described in U.S. Pat. No. 5,993,935 (Rasmussen et al.).

In yet another embodiment, the hydrophobically-derivatized particles are disposed on a surface of a filtration medium. The filter element can be positioned within a housing to provide a filter cartridge. Suitable filtration medium and systems that include a filter cartridge are further described, for example, in U.S. Pat. No. 5,468,847 (Heilmann et al.). Such a filter cartridge can be used, for example, to purify or separate biomolecules. Typically, less rigid particles or smaller porous particles can be utilized within a filter cartridge compared to within a chromatographic column due to the lower pressure drops inherent in the filter cartridge system.

In one aspect of the present disclosure, the hydrophobically-derivatized supports have a reduced amount of ionic groups at the surface of the hydrophobically-derivatized support. Although, not wanting to be bound by theory, it is believed that the hydrophobically-derivatized supports are able to be prepared with even less ionic functionality than the methods currently known in the art. Less ionic functionality on the support surface is thought to be a result of the hydrophobic monomers being prepared and purified prior to any contact with water (i.e., conducting the synthesis of the hydrophobic monomer in organic solvent with no hydrolysis), and conducting the polymerization reactions with monomers that are resistant to hydrolysis.

Azlactones are known to be susceptible to attack by water, which can lead to the formation of carboxyl groups, which may change the selectivity of the surface, imparting both ion-exchange and hydrophilic character to the support's surface. In the present disclosure, the azlactone ring may be opened and covalently bonded to the hydrophobic ligands under non-aqueous conditions, which may limit the generation of ionic groups at the surface of the support. By having fewer competing side reactions, a more pure hydrophobic support can be generated (i.e., less ion-exchange character exhibited by the hydrophobically-derivatized support). Thus, the hydrophobically-derivatized supports of the present disclosure can be more sensitive in hydrophobic interactions and not be influenced by other functional group interactions (e.g. ionic). This provides a more specific separation that is based only on hydrophobic interactions.

Further, the hydrophobically-derivatized supports of the present disclosure display hydrophobicities that are comparable to prior art materials, but comprise much lower hydrophobic ligand densities. For the purposes of this discussion, "ligand density" means micromoles of ligand per milliliter of packed support material. While not wanting to be bound by theory, it is believed that the hydrophobically-derivatized supports of the present disclosure display a more random and even distribution of the hydrophobic ligands on the surface of the support, thus leading to a more efficient utilization of the hydrophobic ligand for interaction with the analyte (e.g., protein) of interest.

In one embodiment, neither the polymerizable mixture nor the hydrophobically-derivatized support comprises a quencher. Because the hydrophobic monomer comprises the hydrophobic ligand covalently bonded to the azlactone, a quencher, such as described in U.S. Pat. No. 5,561,097 (Gleason, et al.) is not needed when forming the hydrophobically-derivatized supports.

Due to the hydrophobic nature of the hydrophobically-derivatized supports, the hydrophobically-derivatized supports may be used for the purification of biological materials, for example, proteins, antibodies, fusion proteins, vaccines, peptides, enzymes, DNA, RNA, or combinations thereof, as well as non-biological molecules with hydrophobic characteristics, in applications such as HIC.

The hydrophobically-derivatized supports of the present disclosure may have advantages over prior art HIC supports. In the present disclosure, an alkenyl azlactone is reacted with a hydrophobic ligand comprising a nucleophile, for example an amine, to form the hydrophobic monomer (or adduct). By using the hydrophobic ligand as part of the hydrophobic monomer in the polymerization step, instead of adding the hydrophobic ligand to a support already comprising an attached azlactone group (such as disclosed in U.S. Pat. Nos. 5,993,935 and 5,561,097), the hydrophobically-derivatized supports of the present disclosure may be achieved with improved uniformity in the distribution of the hydrophobic ligand over the surface of the support and with fewer ionic sites present at the surface of the support. These characteristics may be critical in some HIC applications. The hydrophobically-derivatized supports of the present disclosure may be more resistant to hydrolysis than HIC supports prepared by polymerizing hydrophobic (meth)acrylate esters and/or (meth) acrylamide monomers due to the steric hindrance provided by the —C(R$^1$R$^1$) group interposed between the two carbonyl groups.

EXAMPLES

The following examples are merely for illustrative purposes and are not meant to limit in any way the scope of the appended claims. All parts, percentages, ratios, and the like in the examples are by weight, unless noted otherwise. All raw materials are commercially available or known to those skilled in the art unless otherwise stated or apparent. The structures of all novel hydrophobic monomers were confirmed by H' nuclear magnetic resonance and infrared spectroscopy.

Materials

| Name | Description |
|---|---|
| Vinyl dimethylazlactone | Purchased from SNPE, Inc., Princeton, N.J. |
| N-acryloylmethylalanine | 3M, prepared by the procedure described in U.S. Pat. No. 4,304,705 (Heilmann, et al.) |
| PEG 2,000 | A polyethylene glycol having a molecular weight of 1800-2200 g/mole commercially available from Merck Schuchadt OHG, Hohenbrunn, Germany. |
| PEG 6000 | A polyethylene glycol having a molecular weight of 5000-7000 g/mole commercially available from Merck Schuchadt OHG, Hohenbrunn, Germany. |
| PEG 10,000 | A polyethylene glycol having a molecular weight of 9000-11250 g/mole commercially available from Merck Schuchadt OHG, Hohenbrunn, Germany. |

Preparation of Hydrophobic Monomers

Example 1

The following procedure was used to prepare a 4-phenylbutylamine/VDM adduct. Methyl-tert-butyl ether (MTBE, 100 ml (milliliter)) was added to a 1,000 ml, 3-necked flask, equipped with a condenser, overhead mixing paddle at 400 rotations per minute (rpm), and nitrogen inlet, in an ice bath. Vinyldimethylazlactone (VDM, 10.44 g (gram)) was added to the flask. 4-Phenylbutylamine (10 g) was added to an addition funnel. The bottle in which the 4-phenylbutylamine was stored before addition to the addition funnel was rinsed with portions of MTBE (10 ml total). The MTBE used to rinse the bottle was added to the addition funnel. The 4-phenylbutylamine was added drop-wise over 10-minutes to the flask that contained the VDM. After addition of the 4-phenylbutylamine to the VDM was completed, the addition funnel was rinsed with 10 ml of MTBE. A white precipitate (product) formed almost immediately. The reaction was then allowed to proceed with mixing, under nitrogen, at 0° C. for 60 minutes.

The flask and at least 300 ml of MTBE were transferred to a freezer set at about −20° C. Crystallization of the white precipitate (product) was allowed to occur for 1 to 2 hours. The solid product was filtered on a fritted funnel with three 100 ml washes of the chilled MTBE. The product was dried overnight in a vacuum oven at 60° C. and about 25 inches Hg vacuum. The % yield was about 90%. The purity was checked by silica thin layer chromatography (TLC) with MTBE as the mobile phase. Both of the reactants were much more soluble in MTBE than the product. The melt point of the product, or adduct, was 89-91° C.

Example 2

The following procedure was used to prepare a benzylamine/VDM adduct. A similar procedure as that described for Example 1 above was followed except 49.3 g of benzylamine (instead of 4-phenylbutylamine), 69.9 g of VDM, and 393 ml of diethyl ether (instead of MTBE) were used. The % yield was about 84%.

Example 3

The following procedure was used to prepare a phenethylamine/VDM adduct. A similar procedure as that described for Example 1 above was followed except 43.8 g of phenethylamine (instead of 4-phenylbutylamine), 36.3 g of VDM, and 300 ml of MTBE were used. The % yield was about 94%.

Example 4

The following procedure was used to prepare a phenoxyethylamine/VDM adduct. A similar procedure as that described for Example 1 above was followed except 10 g of phenoxyethylamine (instead of 4-phenylbutylamine), 10.6 g of VDM, and 150 ml of MTBE were used. The % yield was about 92%.

Example 5

The following procedure was used to prepare a 3-phenylpropylamine/VDM adduct. A similar procedure as that described for Example 1 above was followed except 24.7 g of 3-phenylpropylamine (instead of 4-phenylbutylamine), 24.4 g of VDM, and 150 ml of MTBE were used. The % yield was about 77%.

Example 6

The following procedure was used to prepare a butylamine/VDM adduct. A similar procedure as that described for Example 1 above was followed except 43.9 g of butylamine (instead of 4-phenylbutylamine), 83.4 g of VDM, and 500 ml of diethylether (instead of MTBE) were used. The % yield was greater than 85%.

Example 7

The following procedure was used to prepare an octylamine/VDM adduct. A similar procedure as that described for Example 1 above was followed except 77.6 g of octylamine (instead of 4-phenylbutylamine), 83.4 g of VDM, and 650 ml of diethylether (instead of MTBE) were used. The % yield was greater than 85%.

Example 8

The following procedure was used to prepare a dodecylamine/VDM adduct. A similar procedure as that described for Example 1 above was followed except 26.9 g of dodecylamine (instead of 4-phenylbutylamine), 13.9 g of VDM, and 250 ml of diethylether (instead of MTBE) were used. The % yield was greater than 85%.

Example 9

The following procedure was used to prepare an octadecylamine/VDM adduct. A similar procedure as that described for Example 1 above was followed except 26.95 g of octadecylamine (instead of 4-phenylbutylamine), 13.9 g of VDM, and 250 ml of diethylether (instead of MTBE) were used. The product was isolated by evaporating the diethylether solvent, and the % yield was greater than 95%.

Example 10

The following procedure was used to prepare a hexylamine/VDM adduct. A similar procedure as that described for Example 1 above was followed except 60.7 g of hexylamine (instead of 4-phenylbutylamine), 83.4 g of VDM, and 675 of ml diethylether (instead of MTBE) were used. The % yield was greater than 85%.

Example 11

The following procedure was used to prepare a 4-phenyl-1-butanol/VDM adduct. Heptane (50 ml) was added to a 250 ml round bottom flask, equipped with a condenser and magnetic stir bar, in an ice bath. 4-Phenylbutanol (5.00 g) was added to the flask, followed by 5 drops of diazabicycloundecene (DBU) as catalyst. VDM (5.00 g) was added to an addition funnel along with heptane (25 ml). The contents of the dropping funnel were added dropwise over 5 minutes to the flask. After the addition was completed, the mixture was stirred for 45 minutes, then the ice bath was removed. A colorless oil (product) had formed. The reaction was then allowed to proceed with mixing for an additional 2 hours. The heptane supernate was poured off, additional heptane (50 ml) was added, the mixture was stirred another 15 minutes, then left to stand with no stirring for 10 minutes. The heptane supernate again was poured off, and the residual oil was stripped on a rotary evaporator with heating at 35° C. to give 9.28 g of colorless oil (96.5% yield), which crystallized at room temperature.

Preparation of Particles

Example 12

Heptane (174 ml) and 1.4 ml of polymer stabilizer solution ((0.1 g of a polymer comprising a ratio of 92.5 isooctylacrylate to 7.5 VDM, which has been ring opened with ammonia) per ml of toluene) were added to a 1 L Mortonized round bottom flask equipped with an overhead stirrer, thermocouple, reflux condenser, and nitrogen gas inlet. The overhead stirrer was adjusted to a stir rate of approximately 300 rpm and the reaction flask was heated to 35° C. under a slow nitrogen gas purge. Methylene bis-acrylamide (MBA, 11.31 g), 2.09 g of acrylamide (AAm), and 0.60 g of 4-phenylbutylamineNDM adduct (PhBVDM, prepared according to Example 1 above) were added to a 250 ml Erlenmeyer flask equipped with a stir bar. Isopropyl alcohol (62.5 ml) and 42 ml of water were added to dissolve the solids. 10 g of a 50% aqueous solution of PEG 2,000 was then added. Upon dissolution of all solids, sodium persulfate was added to the stirred solution (0.56 g in 3 ml water). The aqueous phase was added to the organic phase and mixed until the reaction mixture reached 35° C. Tetramethylethylenediamine (0.55 ml) was added to initiate the polymerization. The polymerization reaction was stirred for 2 hours while particles formed.

The particles were course filtered and washed twice with acetone (250 ml each), twice with methanol (250 ml each), and then twice with acetone (250 ml each). The resulting particles were transferred to a 500 ml Erlenmeyer flask. Acetone (300 ml) was added to suspend the particles. The suspended particles were sonicated for approximately 15 minutes, then filtered. The resulting particles were classified to a mean particle size of approximately 60 μm (micrometers) using a series of stacked sieves.

Example 13

A similar procedure as that described in Example 12 was followed except PEG 6,000 was added as a porogen additive instead of PEG 2,000.

Example 14

Heptane (348 ml) and 2.8 ml of polymer stabilizer solution were added to a 1 L Mortonized round bottom flask equipped with an overhead stirrer, thermocouple, reflux condenser, and nitrogen gas inlet. The overhead stirrer was adjusted to a stir rate of approximately 300 rpm and the reaction flask was heated to 35° C. under a slow nitrogen gas purge. MBA (21.36 g), 5.50 g of dimethylacrylamide (DMA), and 1.14 g of PhBVDM were added to a 250 ml Erlenmeyer flask equipped with a stir bar. 125 ml of isopropyl alcohol and 84 ml of water were used to dissolve the solids. 20 g of a 50% aqueous solution of PEG 6,000 was then added. Upon dissolution of all solids, sodium persulfate was added to the stirred solution (1.10 g in 6 ml water). The aqueous phase was added to the organic phase and mixed until the reaction reached 35° C. Tetramethylethylenediamine (1.10 ml) was added to initiate the reaction. The polymerization reaction was stirred for 2 hours until particles were formed.

The particles were course filtered and washed twice with acetone (250 ml each), twice with methanol (250 ml each), and twice with acetone (250 ml each). The resulting particles were transferred to a 500 ml Erlenmeyer flask. Acetone (300 ml) was added to suspend the particles. The suspended particles were sonicated for approximately 15 minutes, then filtered. The resulting particles were classified to a mean particle size of approximately 60 μm using a series of stacked sieves.

Example 15

A similar procedure as that described in Example 14 was followed except PEG 10,000 was added as a porogen additive instead of PEG 6,000.

Example 16

Heptane (348 ml), toluene (188 ml) and 1.4 ml of polymer stabilizer solution were added to a 1 L Mortonized round bottom flask equipped with an overhead stirrer, thermocouple, reflux condenser, and nitrogen gas inlet. The overhead stirrer was adjusted to a stir rate of approximately 360 rpm and the reaction flask was heated to 35° C. under a slow nitrogen gas purge. MBA (12.89 g) and 1.11 g of benzylamine/VDM adduct (prepared according to Example 2 above) were added to a 250 ml Erlenmeyer flask equipped with a stir bar. Isopropyl alcohol (65 ml) and 47 ml of water were added to dissolve the solids. Ethylene glycol (25 ml) was then added. Upon dissolution of all solids, sodium persulfate (0.55 g in 3 ml water) was added to the stirred solution. The aqueous phase was added to the organic phase and mixed until the reaction reached 35° C. Tetramethylethylenediamine (0.55 ml) was added to initiate the reaction. The polymerization reaction was stirred for 2 hours until beads formed.

The particles were course filtered and washed twice with acetone (250 ml each), twice with methanol (250 ml each), and then twice with acetone (250 ml each). The resulting particles were transferred to a 500 ml Erlenmeyer flask. Acetone (300 ml) was added to suspend the particles. The suspended particles were sonicated for approximately 15 minutes, and then filtered. The resulting particles were classified to a mean particle size of approximately 65 µm using a series of stacked sieves.

Comparative Example A

Heptane (348 ml), toluene (188 ml) and 1.4 ml of polymer stabilizer solution were added to a 1 L Mortonized round bottom flask equipped with an overhead stirrer, thermocouple, reflux condenser, and nitrogen gas inlet. The overhead stirrer was adjusted to a stir rate of approximately 360 rpm and the reaction flask was heated to 35° C. under a slow nitrogen gas purge. MBA (13.3 g) and N-acryloylmethylalanine (AMA, 0.7 g) were added to a 250 ml Erlenmeyer flask equipped with a stir bar. Isopropyl alcohol (65 ml) and 47 ml of water were added to dissolve the solids. Ethylene glycol (25 ml) was then added. Upon dissolution of all solids, sodium persulfate (0.55 g in 3 ml water) was added to the stirred solution. The aqueous phase was added to the organic phase and mixed until the reaction reached 35° C. Tetramethylethylenediamine (0.55 ml) was added to initiate the reaction. The polymerization reaction was stirred for 2 hrs until particles formed.

The particles were course filtered and washed twice with acetone (250 ml each), twice with methanol (250 ml each), and then twice with acetone (250 ml each). The resulting particles were transferred to a 500 ml Erlenmeyer flask. Acetone (300 ml) was added to suspend the particles. The suspended particles were sonicated for approximately 15 minutes, and then filtered. The resulting particles were classified to a mean particle size of approximately 65 µm using a series of stacked sieves.

Following preparation, the resulting particles were washed thoroughly with acetone and suspended in 500 ml dry dimethylsulfoxide. To this slurry was added acetic anhydride (25 ml) and triethylamine (2 ml). The particles were agitated by rocking for an hour, filtered, and then washed extensively with acetone and MTBE. The resultant azlactone-functional reactive beads were suspended in an aqueous 1 M solution of benzylamine and allowed to react for 1 hour. The beads were then filtered and washed extensively with distilled water.

Experimental Methods

Preparation of Chromatography Column:
Chromatography columns were prepared by slurry packing the exemplary particles into a 3.0 mm×150 mm glass tube supplied by Omifit, Cambridge, CB 1 3HD England. Porous Teflon fits (25 µm average pore size, Small Parts, Inc., Miami Lakes, Fla.) were placed at both ends of the tube to form a chromatography column.

Preparation of Chromatography System:
The chromatography column was assembled in an FPLC (fast protein liquid chromatograph, obtained under the trade designation "AKTA FPLC", GE Healthcare, Uppsala, Sweden equipped with a UV detector and a conductivity detector.

Protein Analysis:
The chromatography column in the chromatography system was equilibrated with a mobile phase of 50 mM (millimolar) sodium phosphate, pH 7 with 1.0 M sodium citrate at a flow rate of 0.088 mL/min. 200 µL (microliter) of a solution containing 0.30 mg (milligram)/ml myoglobin (from Sigma-Aldrich Chemical Company; Milwaukee, Wis.), 0.24 mg/ml β-lactoglobulin (from USB Corporation, Cleveland, Ohio), 0.11 mg/ml lysozyme (from Sigma-Aldrich Chemical Company), and 0.14 mg/ml bovine serum albumin (BSA) (from Sigma-Aldrich Chemical Company) in 50 mM sodium phosphate, pH 7 with 1.0 M sodium citrate was injected onto the chromatography column. A gradient elution (40 column volumes) from the initial buffer condition (high salt) to 50 mM sodium phosphate, pH 7 (low salt) was applied. Using UV detection, the eluent was monitored at a 280 nm (nanometer) wavelength.

Dynamic Binding Capacity Analysis:
The chromatography column in the chromatography system was equilibrated with a mobile phase of 0.6M sodium citrate, pH 6.0. A solution of 2.3 mg/mL of human IgG (hIgG from Equitech, Kerrville, Tex.) in 0.6M sodium citrate at a pH 6.0 was pumped through the chromatography column at a flow rate of 170 cm/hr. Using UV detection, the eluent was monitored at a 280 nm wavelength. The 280 nm absorbance was correlated with IgG concentration. The dynamic binding capacity (DBC) was determined by monitoring the IgG breakthrough (10% of maximum protein concentration eluting from the column).

Analysis Using Particles

Example 17

The particles prepared in Example 12 were packed into a tube to form a chromatography column using the method as described above and an analysis was preformed using the Protein Analysis method as described above. Shown in FIG. 1 is the chromatogram.

Example 18

The particles prepared in Example 13 were packed into a tube to form a chromatography column using the method as described above and an analysis was preformed using the Protein Analysis method as described above. Shown in FIG. 1 is the chromatogram.

Figure 1:
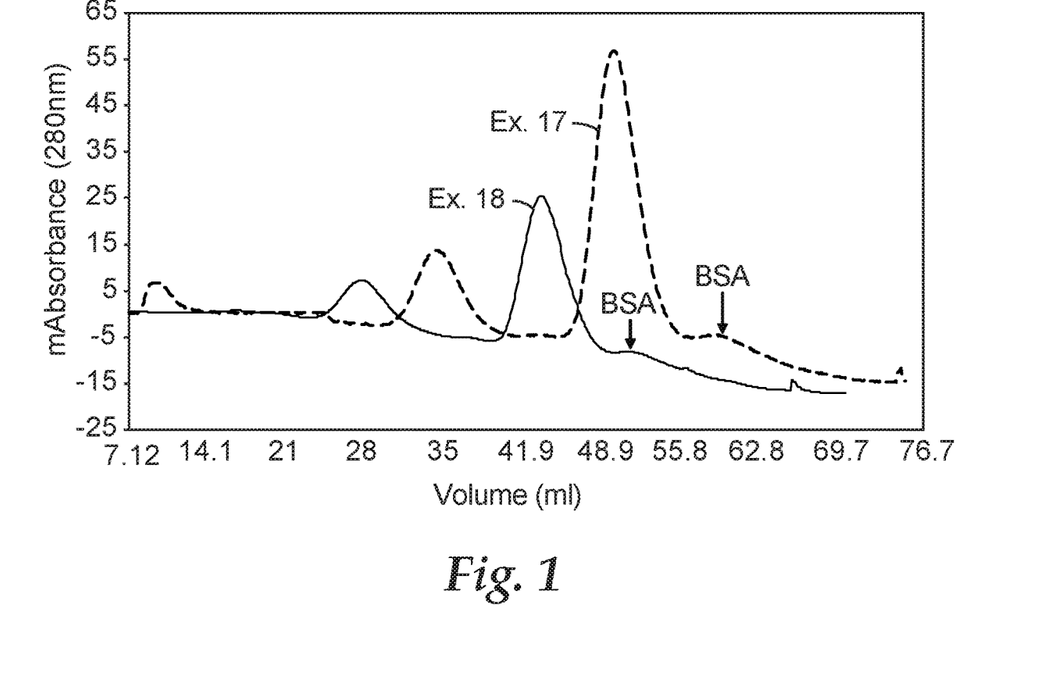
FIG. 1 depicts the hydrophobic interaction chromatograms (absorbance versus elution volume) for Example 17 (Ex. 17) and Example 18 (Ex. 18).

Shown in FIG. 1 is an overlay of the chromatogram from Example 17 (using the particles prepared in Example 12) and Example 18 (using the particles prepared in Example 13). The particles prepared in Examples 12 and 13 were prepared using the same monomer composition and reaction conditions, however, the PEG additive had an effect on the overall hydrophobicity of the particles. As shown in FIG. 1, the particle prepared in Example 12 with PEG 2,000 was more hydrophobic (elution of proteins required a lower salt buffer) than the particle prepared in Example 13 with PEG 6,000. The resolution of BSA was comparable in both Examples 17 and 18, however, the largest eluting peak (a co-elution of β-lactoglobulin and lysozyme) was sharper in Example 17 (the particle prepared with PEG 2,000).

Example 19

Figure 2:
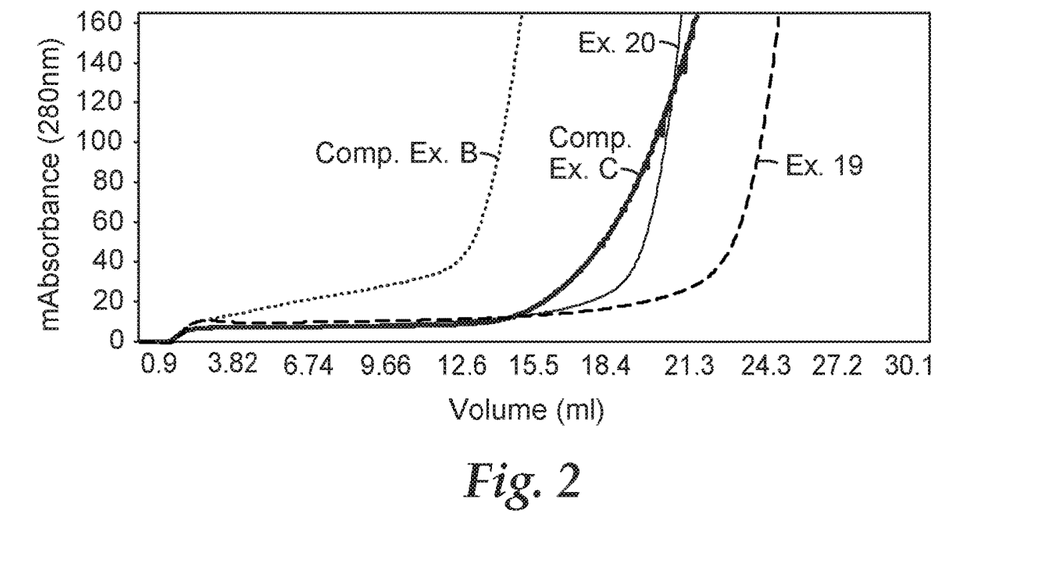
FIG. 2 depicts the dynamic binding capacity chromatograms (absorbance versus elution volume) for Examples 19 (Ex. 19) and Examples 20 (Ex. 20) and Comparative Example B (Comp. Ex. B) and Comparative Example C (Comp. Ex. C).

The particles prepared in Example 12 were packed into a tube to form a chromatography column using the method as described above and an analysis was preformed using the Dynamic Binding Capacity method as described above. Shown in FIG. 2 is the breakthrough curve.

Example 20

The particles prepared in Example 13 were packed into a tube to form a chromatography column using the method as described above and an analysis was preformed using the Dynamic Binding Capacity method as described above. Shown in FIG. 2 is the breakthrough curve.

Comparative Example B

An aromatic HIC media of highly cross-linked 90 µm agarose beads derivatized with phenyl groups via an ether linkage sold under the trade designation "PHENYL SEPHAROSE 6 FAST FLOW (LOW SUB)" commercially available from GE Healthcare, Chalfont St. Giles, United Kingdom were packed into a tube to form a chromatography column using the method as described above and an analysis was preformed using the Dynamic Binding Capacity method as described above. Shown in FIG. 2 is the breakthrough curve.

Comparative Example C

An aromatic HIC media of highly cross-linked 90 µm agarose beads derivatized with phenyl groups via an ether linkage sold under the trade designation "PHENYL SEPHAROSE 6 FAST FLOW (HIGH SUB)" commercially available from GE Healthcare, Chalfont St. Giles, United Kingdom were packed into a tube to form a chromatography column using the method as described above and an analysis was preformed using the Dynamic Binding Capacity method as described above. Shown in FIG. 2 is the breakthrough curve.

FIG. 2 is an overlay of the breakthrough curves for Examples 19 and 20 and Comparative Examples B and C. From the breakthrough curves shown in FIG. 2 the breakthrough was calculated to be as follows: Example 19=58 mg/mL, Example 20=49 mg/mL, Comparative Example B=38 mg/mL, and Comparative Example C=54 mg/mL. The calculated breakthrough indicates that the particles of Example 19 had the most adsorbance of IgG, followed by Comparative Example C, Example 20, and then Comparative Example B. Also shown in FIG. 2 is the profile of the breakthrough for each of the examples, which indicates how the IgG is being adsorbed by the particles/beads. Examples 19 and 20 provided a sharper breakthrough curve (steepness of the exponential growth) than Comparative Example C. Comparative Example B not only had the lowest DBC at 10% breakthrough, but also did not show a flat baseline, indicating that there was inconsistent binding of IgG to the beads. The amount of phenyl per ml of the particles/beads shown in FIG. 2 are as follows: Example 19=14 µmol (micromole) phenyl/ml particle (calculated based on the amount of phenyl monomer used to make the particle and the swell volume of the particle), Example 20=13 µmol phenyl/ml particle (calculated based on the amount of phenyl monomer used to make the particle and the swell volume of the particle), Comparative Example B=25 µmol phenyl/ml particle (taken from product literature), and Comparative Example C=50 µmol phenyl/ml particle (taken from product literature). Based on the data shown in FIG. 2, the particles according to the present disclosure have comparable or better DBC than Comparative Example C, while having substantially less phenyl groups per ml of particle.

Example 21

The particles prepared in Example 14 were packed into a tube to form a chromatography column using the method as described above and an analysis was preformed using the Protein Analysis method as described above. Shown in FIG. 3 is the chromatogram.

Example 22

The particles prepared in Example 15 were packed into a tube to form a chromatography column using the method as described above and an analysis was preformed using the Protein Analysis method as described above. Shown in FIG. 3 is the chromatogram.

Figure 3:
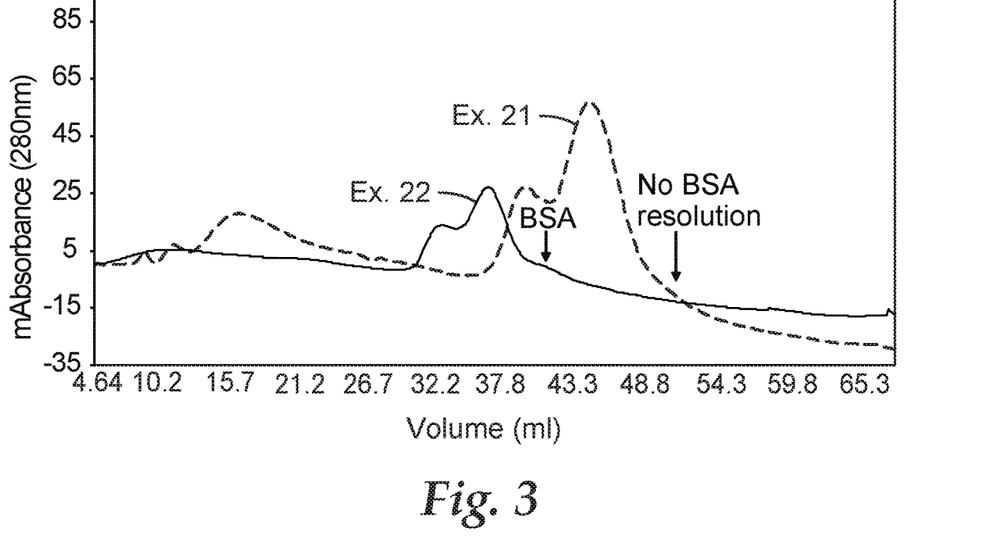
FIG. 3 depicts hydrophobic interaction chromatograms (absorbance versus elution volume) for Example 21 (Ex. 21) and Example 22 (Ex. 22).

Shown in FIG. 3 is an overlay of the chromatogram from Example 21 (using the particles prepared in Example 14) and Example 22 (using the particles prepared in Example 15). The particles prepared in Examples 14 and 15 were prepared using the same monomer composition and reaction conditions, however, the PEG additive had an effect on the overall hydrophobicity of the particles. As shown in FIG. 3, the particle prepared in Example 14 with PEG 6,000 was more hydrophobic than the particle prepared in Example 15 with PEG 10,000. However, the particle prepared in Example 15 with PEG 10,000 was able to resolve BSA from B-lactoglobulin and lysozme, whereas the particle prepared in Example 14 with PEG 6,000 showed no resolution of the BSA peak.

Example 23

The particles prepared in Example 15 were packed into a tube to form a chromatography column using the method as described above and an analysis was preformed using the Dymanic Binding Capacity method as described above. The particle had a calculated DBC of 34 mg/ml. This value is less than the DBC values for the particles prepared with AAm as a comonomer (as shown in Examples 19 and 20 above).

Example 24

The particles prepared in Example 16 were packed into a tube to form a chromatography column using the method as described above and an analysis was preformed using the Protein Analysis method as described above. Shown in FIG. 4 is blow-up of the chromatogram comprising the IgG peak.

Comparative Example D

The particles prepared in Comparative Example A were packed into a tube to form a chromatography column using the method as described above and an analysis was preformed using the Protein Analysis method as described above. Shown in FIG. 4 is blow-up of the chromatogram comprising the IgG peak.

Figure 4:
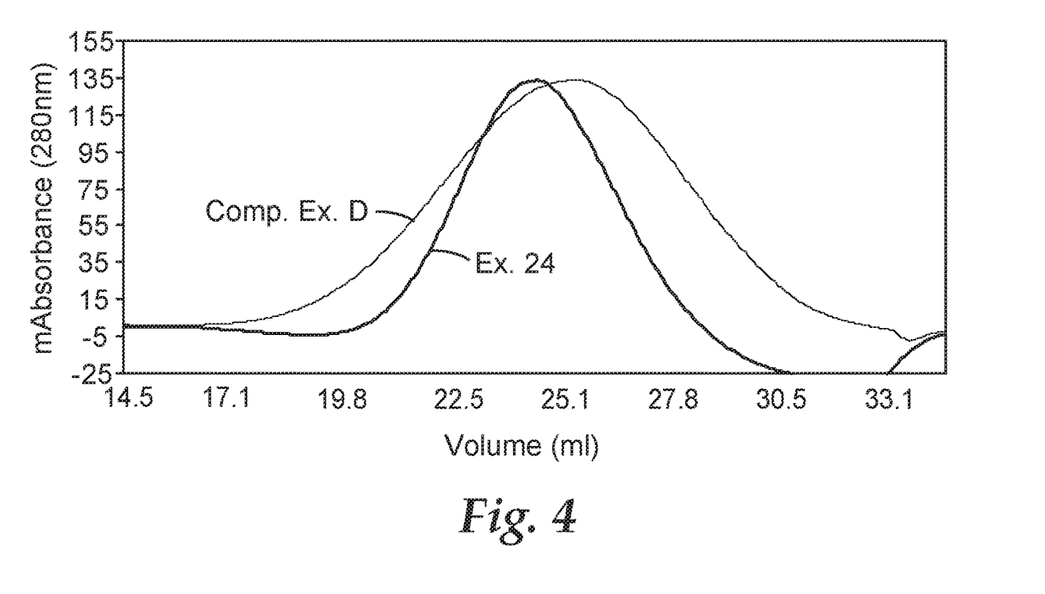
FIG. 4 depicts a selected peak in a hydrophobic interaction chromatogram (absorbance versus elution volume) for Example 24 (Ex. 24) and Comparative Example D (Comp. Ex. D).

Shown in FIG. 4 is an overlay of the IgG peak from Example 24 and Comparative Example D. The particles used in Example 24 and Comparative Example D have the same particle composition; azlactone linkages covalently bonding acrylamide particles with the benzylamine hydrophobic group. Thus, one would expect them to have the same retention time. As shown in FIG. 4, the IgG peak in Example 24 is retained less than in Comparative Example D. Although not wanting to be bound by theory, the increased retention of IgG in Comparative Example D is speculated to be due to the presence of a small amount of negative charge generated by hydrolysis of the azlactone during the reaction with benzylamine. Further, as shown in FIG. 4, the IgG peak in Comparative Example D is broader than that in Example 24, which is also speculated to be indicative of a mixed interaction (e.g. hydrophobic interactions and ion exchange interactions) of the IgG with the stationary phase.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

We claim:

1. A filtration media comprising a porous support with a hydrophobic monomer grafted thereon, the hydrophobic monomer having the structure selected from $CH_2=CHC(O)NHC(CH_3)(CH_3)C(O)NH(CH_2)_4C_6H_5$; $CH_2=CHC(O)NHC(CH_3)(CH_3)C(O)O(CH_2)_4C_6H_5$; $CH_2=CHC(O)NHC(CH_3)(CH_3)C(O)NH(CH_2)_2C_6H_5$; $CH_2=CHC(O)NHC(CH_3)(CH_3)C(O)NH(CH_2)_2OC_6H_5$; $CH_2=CHC(O)NHC(CH_3)(CH_3)C(O)NH(CH_2)_3C_6H_5$; $CH_2=CHC(O)NHC(CH_3)(CH_3)C(O)NH(CH_2)_3CH_3$; $CH_2=CHC(O)NHC(CH_3)(CH_3)C(O)NH(CH_2)_5CH_3$; $CH_2=CHC(O)NHC(CH_3)(CH_3)C(O)NH(CH_2)_7CH_3$; $CH_2=CHC(O)NHC(CH_3)(CH_3)C(O)NH(CH_2)_{11}CH_3$; $CH_2=CHC(O)NHC(CH_3)(CH_3)C(O)NH(CH_2)_{17}CH_3$; or combinations thereof.

2. The filtration media of claim 1, wherein the porous support is flexible.

3. The filtration media of claim 1, wherein the porous support is selected from a woven web, a nonwoven web, a fibrous web, a microporous membrane, a microporous film, and combinations thereof.

4. The filtration media of claim 1, wherein the porous support comprises at least one of polyvinylidene fluoride, polyamides, polyesters, and combinations thereof.

5. A composition comprising a hydrophobic monomer having the structure selected from $CH_2=CHC(O)NHC(CH_3)(CH_3)C(O)NH(CH_2)_4C_6H_5$; $CH_2=CHC(O)NHC(CH_3)(CH_3)C(O)O(CH_2)_4C_6H_5$; $CH_2=CHC(O)NHC(CH_3)C(O)NH(CH_2)_2C_6H_5$; $CH_2=CHC(O)NHC(CH_3)C(O)NH(CH_2)_2OC_6H_5$; $CH_2=CHC(O)NHC(CH_3)C(O)NH(CH_2)_3C_6H_5$; $CH_2=CHC(O)NHC(CH_3)C(O)NH(CH_2)_3CH_3$; $CH_2=CHC(O)NHC(CH_3)C(O)NH(CH_2)_5CH_3$; $CH_2=CHC(O)NHC(CH_3)C(O)NH(CH_2)_7CH_3$; $CH_2=CHC(O)NHC(CH_3)C(O)NH(CH_2)_{11}CH_3$; $CH_2=CHC(O)NHC(CH_3)C(O)NH(CH_2)_{17}CH_3$; or combinations thereof.

* * * * *

UNITED STATES PATENT AND TRADEMARK OFFICE
CERTIFICATE OF CORRECTION

PATENT NO. : 10,807,069 B2
APPLICATION NO. : 15/213572
DATED : October 20, 2020
INVENTOR(S) : Jerald Rasmussen Page 1 of 1

It is certified that error appears in the above-identified patent and that said Letters Patent is hereby corrected as shown below:

In the Specification

Column 2,
Line 38, delete "$(R^2)$" and insert -- $(R^2)_2$ --, therefor.

Column 10,
Line 54, delete "teraphthalate);" and insert -- terephthalate); --, therefor.

Column 15,
Line 59, delete "4-phenylbutylamineNDM" and insert -- 4-phenylbutylamine/VDM --, therefor.

Column 17,
Line 64, delete "CB 1" and insert -- CB1 --, therefor.

In the Claims

Column 21,
Line 27, in Claim 1, delete "$O(CH_2)_4C_6H_5$;" and insert -- $NHCH_2C_6H_5$; --, therefor.

Column 22,
Line 20, in Claim 5, delete "$O(CH_2)_4C_6H_5$;" and insert -- $NHCH_2C_6H_5$; --, therefor.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*